United States Patent
Bertrand et al.

(10) Patent No.: US 8,940,799 B2
(45) Date of Patent: Jan. 27, 2015

(54) ADJUSTING DRUG LOADING IN POLYMERIC MATERIALS

(75) Inventors: William Jeffrey Bertrand, Ventura, CA (US); Patrick Marek, Ventura, CA (US); Drew Amery, Jacksonville, FL (US)

(73) Assignee: Medtronic Xomed, Inc., Jackosnville, FL (US)

( * ) Notice: Subject to any disclaimer, the term of this patent is extended or adjusted under 35 U.S.C. 154(b) by 849 days.

(21) Appl. No.: 12/731,547

(22) Filed: Mar. 25, 2010

(65) Prior Publication Data
US 2011/0237687 A1 Sep. 29, 2011

(51) Int. Cl.
| | |
|---|---|
| *A61K 47/30* | (2006.01) |
| *A61F 13/00* | (2006.01) |
| *A61L 29/04* | (2006.01) |
| *A61L 27/26* | (2006.01) |
| *A61L 27/54* | (2006.01) |
| *A61L 29/16* | (2006.01) |
| *A61L 31/04* | (2006.01) |
| *A61L 31/16* | (2006.01) |

(52) U.S. Cl.
CPC ............. *A61L 29/049* (2013.01); *A61L 27/26* (2013.01); *A61L 27/54* (2013.01); *A61L 29/16* (2013.01); *A61L 31/041* (2013.01); *A61L 31/16* (2013.01); *A61L 2300/60* (2013.01)
USPC ........................ 514/772.3; 424/422

(58) Field of Classification Search
None
See application file for complete search history.

(56) References Cited

U.S. PATENT DOCUMENTS

| | | | |
|---|---|---|---|
| 7,754,272 B2 * | 7/2010 | Rowan et al. | 427/2.1 |
| 2005/0249697 A1 * | 11/2005 | Uhrich et al. | 424/78.37 |
| 2008/0269175 A1 | 10/2008 | Ferris | |
| 2009/0324692 A1 | 12/2009 | Tuominen et al. | |

FOREIGN PATENT DOCUMENTS

| | | |
|---|---|---|
| WO | 97/45066 | 12/1997 |
| WO | WO 9745066 A1 * | 12/1997 |
| WO | 2004/014449 A1 | 2/2004 |

OTHER PUBLICATIONS

Killian et al. "Effect of Gamma Sterilization on Select TPE Materials" Jan. 2008, pp. 1-13. Accessed online at http://medicaldesign.com/Whitepapers/TPE_Gamma_Sterilization_White_Paper.pdf on Nov. 16, 2012.*
Dow Corning Class VI Elastomers (C6-235, C6-250, C6-265), Dow Corning Corporation, May 28, 2008, (5 pages).
PCT Search Report mailed Jun. 15, 2011 (11 pages).
Notification of Transmittal of International Preliminary Report on Patentability (PCT/US11/29388) mailed Jan. 10, 2013 (8 pages).

* cited by examiner

*Primary Examiner* — Carlos Azpuru
*Assistant Examiner* — Casey Hagopian
(74) *Attorney, Agent, or Firm* — Dicke, Billig & Czaja, PLLC

(57) ABSTRACT

Drug loading of polymeric materials can be adjusted by selection of materials and/or adjusting processing steps in formation of an implantable drug-loaded device.

5 Claims, 3 Drawing Sheets

ADJUSTING DRUG LOADING IN POLYMERIC MATERIALS

FIELD

This disclosure relates, inter alia, to implantable medical devices, polymeric materials, and therapeutic agents. More particularly, it relates to systems, devices and methods for incorporating therapeutic agents into polymeric materials that form a part of or may be disposed in proximity to implantable medical devices.

BACKGROUND

Drugs (e.g., including one or more therapeutic agents) are loaded into a variety of polymeric materials, which may serve as a vehicle for delivering the drug to a patient. Often the polymeric materials into which drugs are loaded are a part of or otherwise associated with implantable medical devices. For example, polymeric vascular catheters are commercially available with anti-infective agents loaded into the polymeric material forming the catheter body. The anti-infective agents prevent infection associated with implanting the catheters. In addition, it has been proposed that drug loaded polymeric boots to be disposed about implantable medical devices, such as cardiac defibrillators, infusion devices and implantable neurostimulators, may be similarly effective at preventing infection. However, the amount of drug that may be loaded into polymeric materials is currently limited.

SUMMARY

It has been found that drug loading capacity can be adjusted as a function of hardness of a polymeric material. Additionally, it has been found that drug loading capacity can be adjusted by impregnating drug into the polymeric material prior to a post-cure processing step.

Adjusting the loading capacity of polymeric materials will increase the design flexibility of drug-loaded polymeric boots, sheaths, discs, catheters and the like. In particular, an amount of drug loaded into polymeric materials can be readily controlled. These and other advantages will be readily understood from the following detailed descriptions when read in conjunction with the accompanying drawings.

DETAILED DESCRIPTION

Figure 1:
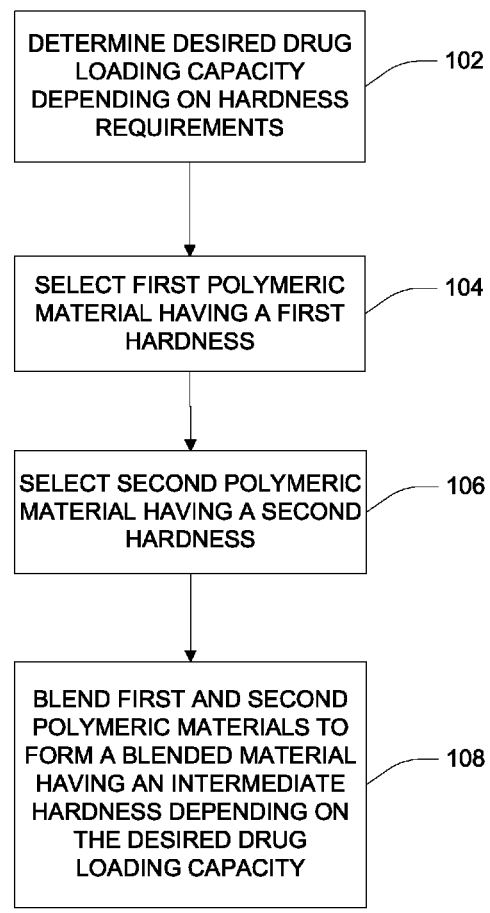
FIG. 1 is a flow diagram of a method for selecting a drug loading capacity of an implantable medical device.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "therapeutic agent" means a molecule, such as a large molecule (e.g., a peptide or nucleic acid or derivatives thereof) or a small molecule, that may result in a beneficial effect when administered to a subject, such as a human.

Reference herein to any chemical compound should be construed as reference to the compound and any pharmaceutically acceptable salts, solvates, hydrates, isomers, and polymorphs thereof.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure relates, among other things, to implantable medical devices, polymeric materials, and incorporation of agents into polymeric materials. It has been found that a tradeoff exists between hardness of a polymeric material and associated drug loading capacity. Moreover, it has been found that for therapeutic agents capable of withstanding post-cure process temperatures, the agents can be incorporated into the polymeric material prior to a post-cure processing step so as to increase drug loading capacity compared with incorporating agents after the post-cure processing step. Additionally, the polymeric material, prior to a post-cure processing step, can be "overloaded" (i.e., with more than the desired amount) with the desired agent so as to result in the proper concentration after post curing has caused some degradation in the agent.

Polymers

Any suitable polymeric material may be used in accordance with the teachings presented herein. The polymeric material may be any suitable shape and may take any suitable form. For example, the polymeric material may be in the form of a tube, sheath, sleeve, boot, disc, or the like. The polymeric material may be extruded, molded, or otherwise formed. Examples of commonly used suitable polymeric materials include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE).

The polymeric material may be biodegradable, such as synthetic or natural bioabsorbable polymers. Synthetic bioabsorbable polymeric materials that can be used to form the coating layers include poly(L-lactic acid), polycaprolactone, poly(lactide-co-glycolide), poly(ethylene-vinyl acetate), poly(hydroxybutyrate-covalerate), polydioxanone, polyorthoester, polyanhydride, poly(glycolic acid), poly(D, L-lactic acid), poly(glycolic acid-co-trimethylene carbonate), polyphosphoester, polyphosphoester urethane, poly (amino acids), cyanoacrylates, poly(trimethylene carbonate), poly(iminocarbonate), copoly(ether-esters) such as PEOI PLA, polyalkylene oxalates, polyphosphazenes, andpolyarylates including tyrosine-derived polyarylates. According to another exemplary embodiment, the polymeric materials can be natural bioabsorbable polymers such as, but not limited to, fibrin, fibrinogen, cellulose, starch, collagen, and hyaluronic acid. "Biodegradable", "bioerodable", "bioabsorbable", and the like are used herein interchangeably.

In various embodiments, the polymeric material is an elastomeric polymeric material. Examples of elastomeric polymeric materials include polyisoprene, polyisobutylene, polystyrene, poly(vinyl chloride), polyurethane, silicone, ethylene-propylene elastomers, styrene-1,3-butadiene, acrylonitrile-1,3-butadiene, isobutylene-isoprene, and the like.

The polymeric material may be in the form of a boot designed to be placed around an implantable medical device or a disc. The polymeric material with which one or more therapeutic agent has been associated may be placed in a subcutaneous pocket or may be placed on or about an implantable medical device. In various embodiments, the polymeric material is bonded, adhered to, coated on, or otherwise attached to the implantable medical device. In other embodiments, the polymeric material is formed into a polymeric shunt catheter, vascular catheter and includes various features such as apertures, fenestrations, shapes, markings, connections and the like.

Therapeutic Agent

Any therapeutic agent may be associated with a polymeric material in accordance with the teachings presented herein. If a therapeutic agent loaded polymeric material is associated with an implantable medical device, it may be desirable to treat or prevent infections, inflammation, or proliferation associated with implantation of a medical device. Accordingly, it may be desirable to associate one or more anti-infective agent, one or more anti-inflammatory agent, one or more anti-proliferative agent, or a combination thereof with the polymeric material. In some circumstances, it may be desirable to deliver a local anesthetic. Additional therapeutic agents that may be associated with a polymeric material, regardless of whether the polymeric material is associated or to be associated with an implantable medical device, will be readily evident to one of skill in the art. A brief summary of some non-limiting classes of therapeutic agents that may be used follows.

1. Anti-Infective Agents

Any anti-infective agent may be used in accordance with various embodiments. As used herein. "anti-infective agent" means an agent that kills or inhibits the growth of an infective organism, such as a microbe or a population of microbes. Anti-infective agents include antibiotics and antiseptics.

A. Antibiotic

Any antibiotic suitable for use in a human may be used in accordance with various embodiments of the invention. As used herein, "antibiotic" means an antibacterial agent. Many antibiotics have limited effect against microbes other than bacteria. The antibacterial agent may have bacteriostatic and/ or bacteriocidal activities.

Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericinB), azoles (e.g. fluconazole) and betalactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, which is herein incorporated by reference in its entirety, may also be used. One of ordinary skill in the art will recognize other antibiotics that may be used.

If the polymeric material is associated with or to be associated with an implantable medical device, it is desirable that the selected antibiotic(s) kill or inhibit the growth of one or more bacteria that are associated with infection following surgical implantation of a medical device. Such bacteria are recognized by those of ordinary skill in the art and include *Staphylococcus aureus, Staphylococcus epidermis*, and *Escherichia coli*. Preferably, the antibiotic(s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that antimicrobial agents having different mechanisms of action and/or different spectrums of action may be most effective in achieving such an effect. In an embodiment, a combination of rifampin and micocycline is used. In an embodiment, a combination of rifampin and clindamycin is used.

B. Antiseptic

Any antiseptic suitable for use in a human may be used in accordance with various embodiments. As used herein, "antiseptic" means an agent capable of killing or inhibiting the growth of one or more of bacteria, fungi, or viruses. Many antiseptics, such as disinfectants, are effective against two or more of, or all of, bacteria, fungi, and viruses. Nonlimiting examples of antiseptics include hexachlorophene, cationic bisiguanides (i.e. chlorhexidine, cyclohexidine) iodine and iodophores (i.e. povidone-iodine), parachloro-meta-xylenol, triclosan, furan medical preparations (i.e. nitrofurantoin, nitrofurazone), methenamine, aldehydes (glutaraldehyde, formaldehyde), silver-containing compounds (silver sulfadiazine, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

If the polymeric material is associated with or to be associated with an implantable medical device (e.g., the polymeric material forms a part of the device, such as a catheter or lead, is to be disposed about, coated on, or otherwise adhered to the device, or is placed in proximity to the device after implantation), it is desirable that the antiseptic(s) selected kill or inhibit the growth of one or more microbe that are associated with infection following surgical implantation of a medical device. Such microbes are recognized by those of ordinary skill in the art and include *Staphylococcus aureus, Staphylococcus epidermis, Escherichia coli, Pseudomonas auruginosa*, and *Candidia*.

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action and/or different spectrums of action may be most effective in achieving such an effect. In a particular embodiment, a combination of chlorohexidine and silver sulfadiazine is used.

C. Antiviral

Any antiviral agent suitable for use in a human may be used in accordance with various embodiments of the invention. Nonlimiting examples of antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. One of ordinary skill in the art will recognize other antiviral agent that may be employed in accordance with this disclosure.

To enhance the likelihood that viruses will be killed or inhibited, it may be desirable to combine two or more antiviral agents. It may also be desirable to combine one or more antiseptics with one or more antiviral agent.

D. Anti-Fungal

Any anti-fungal agent suitable for use in a human may be used in accordance with various embodiments of the invention. Nonlimiting examples of anti-fungal agents include amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione. One of ordinary skill in the art will recognize other anti-fungal agents that may be employed in accordance with this disclosure.

To enhance the likelihood that viruses will be killed or inhibited, it may be desirable to combine two or more anti-fungal agents. It may also be desirable to combine one or more antiseptics with one or more anti-fungal agent.

2. Anti-Inflammatory Agents

Any anti-inflammatory agent suitable for use in a human may be used in accordance with various embodiments. Non-limiting examples of anti-inflammatory agents include steroids, such as cortisone, hydrocortisone, prednisone, dexamethasone, methyl-prednisilone, and derivatives thereof, and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

3. Local Anesthetics

Any local anesthetic agent suitable for use in a human may be used in accordance with various embodiments. Non-limiting examples of local anesthetics agents include lidocaine, prilocalne, mepivicaine, benzocaine, bupivicaine, amethocaine, lignocaine, cocaine, cinchocaine, dibucaine, etidocaine, procaine, veratridine (selective c-fiber blocker) and articaine.

4. Other Pharmacological Agents

Non-limiting examples of other pharmacological agents that may be used include: beta-radiation emitting isotopes, beclomethasone, fluorometholone, tranilast, ketoprofen, curcumin, cyclosporin A, deoxyspergualin, FK506, sulindac, myriocin, 2-aminochromone (U-869831, colchicines, pentosan, antisense oligonucleotides, mycophenolic acid, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin; Antineoplastic/antiangiogenic agents, such as antimetabolite agents, alkylating agents, cytotoxic antibiotics, vinca alkaloids, mitosis inhibitors, platinum compounds, tissue growth factor inhibitors, cisplatin and etoposide; Immunosuppressant agents, such as cyclosporine A, mycophenolic acid, tacrolimus, rapamycin, rapamycin analogue (ABT-578) produced by Abbott Laboratories, azathioprine, recombinant or monoclonal antibodies to interleukins, T-cells, B-cells and/or their receptors; Anticoagulants, such as heparin and chondroitin sulfate; Platelet inhibitors such as ticlopidine; Vasodilators such as cyclandelate, isoxsuprine, papaverine, dipyrimadole, isosorbide dinitrate, phentolamine, nicotinyl alcohol, co-dergocrine, nicotinic acid, glycerol trinitrate, pentaerythritol tetranitrate and xanthinol; Thrombolytic agents, such as stretokinase, urokinase and tissue plasminogin activators; Analgesics and antipyretics, such as the opioid analgesics such as buprenorphine, dextromoramide, dextropropoxyphene, fentanyl, alfentanil, sufentanil, hydromorphone, methadone, morphine, oxycodone, papavereturn, pentazocine, pethidine, phenopefidine, codeine dihydrocodeine; acetylsalicylic acid (aspirin), paracetamol, and phenazone; and Antiproliferative agents such as QP-2 (taxol), paclitaxel, rapamycin, tacrolimus, everolimus, actinomycin, methotrexate, angiopeptin, vincristine, mitocycin, statins, C-MYC antisense, sirolimus, restenASE, 2-chloro-deoxyadenosine, PCNA (proliferating cell nuclear antigent) ribozyme, batimastat, prolyl hydroxylase inhibitors, halofuginone, C-proteinase inhibitors, and probucol; and combinations and/or derivates thereof.

In various embodiments, a steroid (e.g., dexamethasone), a cell antiproliferative agent (e.g., rapamycin) and a radioactive substance are associated with a polymeric material.

A therapeutic agent may be present in the polymeric material at any suitable concentration. For example, a therapeutic agent may comprise 0.1% to 50%, 0.1% to 20%, 0.1% to 5%, 1% to 10%, etc. of the weight of the article.

Solvents

Any suitable solvent may be used to load the therapeutic agent into the polymeric material. Furthermore, any solvent-mediated process may be used to incorporate therapeutic agent into the polymeric material. For example, a therapeutic agent may be impregnated into the polymeric material by swelling the polymer in a solution of an appropriate solvent. Generally it is desirable that the therapeutic agent be soluble in the solvent and that the solvent is capable of swelling the polymer. One of skill in the art will readily understand which solvents are capable of dissolving the therapeutic agent and swelling the polymeric material. Regardless of the process or solvent used to incorporate or associate the therapeutic agent with the polymeric material, it is desired that the therapeutic agent be incorporated or associated in an amount effective to produce its intended therapeutic effect when administered to a subject.

FIG. 1 is a flow diagram of a method for selecting a polymeric material to be utilized in an implantable medical device based on a tradeoff of increased drug loading capacity versus reduced hardness of the polymeric material. Method 100 begins at step 102, wherein a desired drug loading capacity is determined for the device depending on hardness requirements for the implantable medical device. A tradeoff between the desired drug loading capacity and desired physical characteristics exist in forming a drug loaded implantable medical device. In particular, it has been found that a relationship exists between a hardness of the polymeric material and the drug loading capacity. For example, Table 1 below illustrates durometer values and associated drug loading capacity of clindamycin.

TABLE 1

| Durometer (shore A) | Clindamycin capacity, wt. % |
|---|---|
| 44 | 0.163 |
| 50.5 | 0.155 |
| 57 | 0.11 |

Based on Table 1, a linear regression analysis can be performed in order to predict drug loading capacity as a function of hardness of a polymeric material. Given these predicted values, devices can be designed with a desired loading loading capacity. As many manufacturers of silicone elastomeric raw materials provide their raw materials in various hardness ratings from soft to firm, the raw materials can be blended to form a material of intermediate hardness and thus a selected drug loading capacity. For example, Dow Corning Corporation of Midland, Mich., provides elastomers in a soft hardness (with a nominal 35 shore A durometer), a medium hardness (with a nominal 50 shore A durometer) and a firm hardness (nominally 65 shore A durometer). As desired, these materials may be blended to achieve intermediate hardness. With reference to method 100, step 106 includes selecting a first polymeric material having a first hardness. Next, a second polymeric material having a second hardness is selected at step 108. At step 110, the first and second polymeric materials are blended to achieve an intermediate hardness with a predetermined, selected drug loading capacity.

Figure 2:
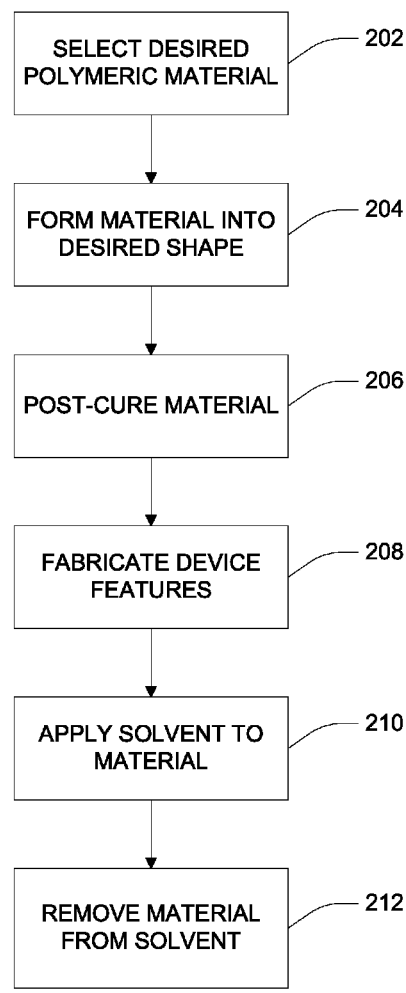
FIG. 2 is a flow diagram of a first embodiment of a method for forming an implantable drug-loaded medical device.
Figure 3:
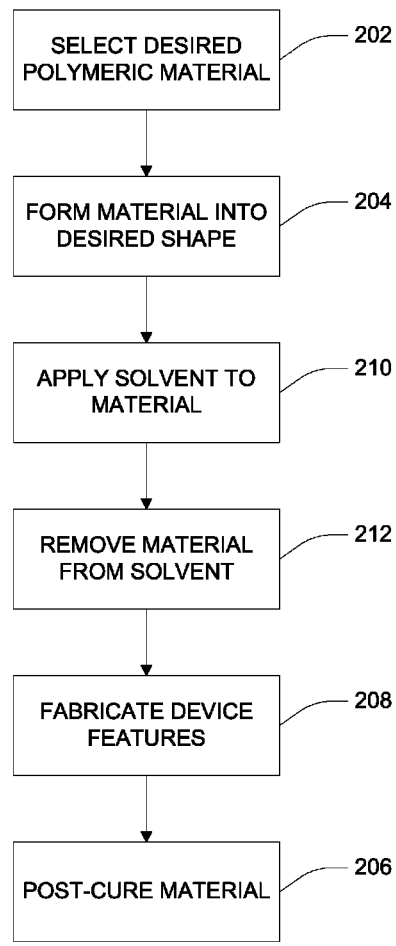
FIG. 3 is a flow diagram of a second embodiment of a method for forming an implantable drug-loaded medical device.

Once the desired polymeric material has been selected, an implantable medical device can then be formed using various methods. FIGS. 2 and 3 illustrate two exemplary methods for forming an implantable medical device with a therapeutic agent impregnated therein. Method 200 in FIG. 2 and Method 300 in FIG. 3 include similar steps that are similarly numbered, yet performed in a different order. Methods 200 and 300 are illustrative only, and those skilled in the art will recognize that other steps can further be utilized within the general framework of methods 200 and 300.

Method 200 begins at step 202 wherein the desired polymeric material is selected, for example using method 100 of FIG. 1 or another method as desired. If method 100 of FIG. 1 is used, the steps discussed below are applicable to the blended polymeric material formed at step 108 as discussed above. Next, at step 204, the polymeric material is formed into a desired shape. For example, the shape can be a tube that is extruded, the shape can be a boot, etc. Next, at step 206 the polymeric material is subjected to a post-curing process. For example, the post-curing process can involve vulcanizing the polymeric material, exposing the material to high temperatures in an oven, etc. that may otherwise be specified by a raw material provider or adjusted depending upon desired characteristics of a completed device. Next, at step 208, device features are fabricated as desired. For example, a catheter can include various holes, structures, fenestrations, shapes, markings and the like. Once the features are fabricated, method 200 proceeds to step 210, wherein the solvent is applied to the material. In one embodiment, the material can be submerged in the solvent so as to impregnate the material with a therapeutic agent. Next, at step 212, the material is removed from the solvent and dried. At this point, the material forms a drug-loaded device that is ready for packaging and shipping.

EXAMPLE A

In one example (Example A), methods 100 and 200 were used to form a shunt catheter. It was determined that a shunt catheter having a 57 durometer shore A hardness would provide a suitable hardness for use of the shunt catheter. Additionally, it was desired to have a 0.015 weight % of clindamycin and a 0.054 weight % of rifampicin loaded into the shunt catheter. However, it was found that the shunt catheter did not have the desired capacity for which to load the required weight % of the drug clindamycin. In turn, using a softer 44 durometer shore A material would allow proper loading, but was too soft for the desired hardness of the shunt catheter. By utilizing method 100, a 50/50 blend (i.e., equal amounts) of 57 durometer material and 44 durometer material was chosen and blended according to method 100. After blending and then fully post-curing the material, final catheter fabrications were made, such as holes, tip forming and markings. After catheter fabrication, the material was subject to soaking in a chloroform solvent containing both rifampicin and clindamycin for approximately 45-60 minutes. The solvent was drained off, the catheter was dried and packaged and finally sterilized by steam. The rifampicin, initially at about 0.15-0.17% by weight before steam sterilization, is degraded about 60% to a final target concentration of 0.054 weight %. Clindamycin is more stable and degrades only about 10%. After sterilization, the shunt catheter had about 0.15% clindamycin and 0.054% rifampicin with a suitable intermediate hardness.

In FIG. 3, the post-curing processing step 206 moves to the end of method 300 and the solvent application step 210 is performed after forming of the material into a desired shape (step 204). In method 300, as long as the therapeutic agent utilized in the solvent application step 210 is equipped to withstand temperatures applied during the post-curing processing step 206, or sufficient quantities can be loaded before post-curing to compensate for degradation. The solvent is applied before post-curing and the post-curing step 206 alters the durometer of the polymeric material.

EXAMPLE B

In another example, (Example B) method 300 was used to form a general catheter without holes, tip forming or markings. In this example, the material used was 100% of 57 durometer shore A material. A desired amount of clindamycin was able to be loaded into the material by applying the solvent to the material before post-curing. In this particular example, the catheter fabrication steps of tip forming and marking are not performed, as these fabrication steps expose the catheter to heat t, thereby reducing the clindamycin capacity. However, a higher hardness and drug loading capacity can be achieved for the catheter by applying the solvent to the material prior to post-curing.

Thus, embodiments of ADJUSTING DRUG LOADING IN POLYMERIC MATERIALS are disclosed. One skilled in the art will appreciate that the present invention can be practiced with embodiments other than those disclosed. The disclosed embodiments are presented for purposes of illustration and not limitation, and the present invention is limited only by the claims that follow.

Although the present disclosure has been described with reference to preferred embodiments, workers skilled in the art will recognize that changes can be made in form and detail without departing from the spirit and scope of the present disclosure.

What is claimed is:

1. A method of forming an implantable medical device, comprising:
   forming an elastomeric polymeric material into a shape of the implantable medical device;
   applying a solvent to the polymeric material so as to load the polymeric material with a therapeutic agent; and
   subjecting the polymeric material to a post-curing process including vulcanizing the polymeric material after applying the solvent to the polymeric material, wherein the post-curing process alters a hardness for the polymeric material.

2. The method of claim 1, further comprising:
   fabricating features of the implantable medical device into the polymeric material.

3. The method of claim 1, further comprising:
   selecting a predetermined drug loading capacity for the implantable medical device;
   selecting a first polymeric material having a first hardness;
   selecting a second polymeric material having a second hardness different from the first hardness; and
   blending the first polymeric material with the second polymeric material to obtain a blended polymeric material having the selected predetermined drug loading capacity.

4. The method of claim 1, wherein the post-curing process includes exposing the polymeric material to heat within an oven.

5. The method of claim 1, further comprising forming at least one of a hole, a tip and a marking into the polymeric material.

* * * * *